US007531567B2

(12) United States Patent
Täger et al.

(10) Patent No.: US 7,531,567 B2
(45) Date of Patent: May 12, 2009

(54) USE OF A MEDICAMENT CONTAINING AN EFFECTOR OF THE GLUTATHIONE METABOLISM TOGETHER WITH α-LIPOIC ACID IN KIDNEY REPLACEMENT THERAPY

(75) Inventors: Michael Täger, Heinrichsberg (DE); Siegfried Ansorge, Hohenwarthe (DE); Gerhard Fries, Wahlitz (DE); Dieter Koegst, Wahlitz (DE)

(73) Assignee: Serumwerk Bernburg AG, Bernburg (DE)

( * ) Notice: Subject to any disclaimer, the term of this patent is extended or adjusted under 35 U.S.C. 154(b) by 0 days.

(21) Appl. No.: 10/479,080

(22) PCT Filed: May 24, 2002

(86) PCT No.: PCT/DE02/01991

§ 371 (c)(1),
(2), (4) Date: Nov. 26, 2003

(87) PCT Pub. No.: WO02/096414

PCT Pub. Date: Dec. 5, 2002

(65) Prior Publication Data

US 2004/0127550 A1    Jul. 1, 2004

(30) Foreign Application Priority Data

May 28, 2001    (DE) ................................ 101 25 883

(51) Int. Cl.
*A61K 31/385*    (2006.01)
*A61K 31/403*    (2006.01)

(52) U.S. Cl. ........................................ 514/412; 514/442
(58) Field of Classification Search .................. 514/412, 514/440; 548/533, 452; 549/39
See application file for complete search history.

(56) References Cited

U.S. PATENT DOCUMENTS 5,650,429 A    7/1997    Conrad et al.
6,518,300 B2    2/2003    Alken et al.

FOREIGN PATENT DOCUMENTS

| CA | 2 073 084 | 1/1993 |
|---|---|---|
| DE | 35 30 761 A1 | 3/1987 |
| DE | 38 04 858 A1 | 8/1989 |
| DE | 43 43 592 C2 | 6/1995 |
| DE | 44 20 102 A1 | 12/1995 |
| DE | 44 47 599 C2 | 7/1996 |
| DE | 198 06 354 A1 | 8/1999 |
| EP | 0 427 247 B1 | 5/1991 |
| EP | 0 530 446 B1 | 3/1993 |
| EP | 0 812 591 A2 | 12/1997 |
| GB | 2 239 242 A | 6/1991 |
| WO | WO 96/18370 | 6/1996 |
| WO | WO 96/33704 | 10/1996 |
| WO | WO 97/37629 | 10/1997 |
| WO | WO 00/61537 | 10/2000 |
| WO | WO 01/05378 A1 | 1/2001 |

OTHER PUBLICATIONS

Derick et al., Biochem. Biophy. Research Comm. (1995), vol. 207, No. 1, pp. 258-264.*
Biewenga, et al., "The Pharmacology of the Antioxidant Lipoic Acid" *Gen. Pharmac.* vol. 29, No. 3, 1997, missing p. 316.
Martin-Mateo et al., "Oxidative Stress and Enzyme Activity in Ambulatory Renal Patients Undergoing Continuous Peritoneal Dialysis", *Renal Failure* (1998), pp. 117-124, vol. 20(1).
Jain et al., "Glutathione Metabolism in Newborns: Evidence for Glutathione Deficiency in Plasma, Bronchoalveolar Lavage Fluid, and Lymphocytes in Prematures", *Pediatric Pulmonology* (1995), pp. 160-166, vol. 20.
Gibbs, et al., "Ambroxol inhibits the release of histamine, leukotrienes and cytokines from human leukocytes and mast cells" Inflamm. Res. 48 (1999) p. 86 only (pp. 86-93 previously provided in Apr. 13, 2004 Supplemental Information Disclosure).
Bains, et al., Full-length review "Neurodegenerative disorder in humans: the role of glutathione in oxidative stress-mediated neuronal death" Brian Research Reviews 25 (1997) pp. 335-358.
Sian, et al., "Alterations in Glutathione Levels in Parkinson's Disease and Other Neurodegenerative Disorders Affecting Basal Ganglia" American Neurological Association, 1994; 36, pp. 348-355.
Güler, et al., "Total antioxidant status, lipid parameters, lipid peroxidation and glutathione levels in patients with acute myocardial infarction" Medical Science Research, 1998; 26, pp. 105-106.
Reise, et al., Glutathione and neonatal lung disease Clinica Chimica Acta, 265 (1997), pp. 113-119.
Laurent, et al., clinical investigations in critical care "Oxidant-Antioxidant Balance in Granulocytes During ARDS Effect of N-Acetylcysteine" Chest, Jan. 1996; vol. 109, pp. 163-166.
Täger, et al., "Evidence of a Defective Thiol Status of Alveolar Macrophages From COPD Patients and Smokers" Free Radical Biology & Medicine, 2000; vol. 29, pp. 1160-1165.
Scott, et al., "Thalassaemic erythrocytes: cellular suicide arising from iron and glutathione-dependent oxidation reactions?" British Journal of Haematology, 1995; 91, pp. 811-819.
Yamasoba, et al., "Role of glutathione in protection against noise-induced hearing loss" Brain Research 784 (1998), pp. 82-90 with cover page (2 pages).
Sido, et al., "Impairment of intestinal glutathione synthesis in patients with inflammatory bowel disease" Gut, 1998: 42, pp. 485-492.
De Mattia, et al., "Influence of Reduced Glutathione Infusion on Glucose Metabolism in Patients With Non-Insulin-Dependent Diabetes Mellitus" Metabolism, vol. 47, No. 8, 1998, pp. 993-997.
Herzenberg, et al., "Glutathione deficiency is associated with impaired survival in HIV disease" Proc. Natl. Acad. Sci. USA, vol. 94, Mar. 1997, pp. 1967-1972 Medical Sciences.
Ghibelli, et al., "Rescue of cells from apoptosis by inhibition of active GSH extrusion" The FASEB Journal, vol. 12, Apr. 1998, pp. 479-486.

(Continued)

*Primary Examiner*—Taofiq A Solola
(74) *Attorney, Agent, or Firm*—Christie, Parker & Hale, LLP.

(57) ABSTRACT

The invention relates to the use of the combination of n-lipoic acid and effectors of the glutathione metabolism for the treatment of disturbances of the cellular thiol status and accompanying disorders in kidney replacement therapy.

21 Claims, 7 Drawing Sheets

OTHER PUBLICATIONS

Burger, et al., "In vitro Differentiation and Characterization of Human Peritoneal Macrophages from CAPD-Peritonitis Patients" Immunobiol., vol. 200 (1999) pp. 62-76.
Ziegler, et al., "Treatment of symptomatic diabetic peripheral neuropathy with the anti-oxidant α-lipoic acid" Diabetologia (1995) 38, pp. 1425-1432.
Inoue, et al., "Lack of effect of CS-045, a new antidiabetic agent, on insulin secretion in the remnant pancreas after 90% pancreatectomy in rats" Diabetes Research and Clinical Practice 27 (1995), pp. 19-26.
Ziegler, et al., "Treatment of Symptomatic Diabetic Polyneuropathy With the Antioxidant α-Lipoic Acid" Diabetes Care, vol. 22, No. 8, Aug. 1999, pp. 1296-1301.
Biewenga, et al., "The Role of Lipoic Acid in the Treatment of Diabetic Polyneuropathy" Drug Metabolism Review, 29(4), 1997, pp. 1025-1054.
Packer, et al., "Alpha-Lipoic Acid as a Biological Antioxidant" Free Radical Biology & Medicine, vol. 19, No. 2, 1995, pp. 227-250.
Pan, et al., "D,L-S-Methyllipoic Acid Methyl Ester, a Kinetically Viable Model for S-Protonated Lipoic Acid as the Oxidizing Agent in Reductive Acyl Transfers Catalyzed by the 2-Oxoacid Dehydrogenase Multienzyme Complexes" Biochemistry 1998, 37, pp. 1357-1364.
Merin, et al., "α-Lipoic acid blocks HIV-1 LTR-dependent expression of hygromycin resistance in the THP-1 stable transformants" FEBS Letters 394 (1996), pp. 9-13.
Burkart, et al., "Dihydrolipoic acid protects pancreatic islet cells from inflammatory attack" Agents Actions 38 (1993), pp. 60-65.
Biewenga, et al., "The Pharmacology of the Antioxidant Liopoic Acid" Gen. Pharmac. vol. 29, No. 3, 1997, pp. 315, 317-331.
Gillissen, et al., "Characterization of N-acetylcysteine and ambroxol in anti-oxidant therapy" Respiratory Medicine (1998) 92, pp. 609-623.
Teramoto, et al., "Effects of Ambroxol on Spontaneous or Stimulated Generation of Reactive Oxygen Species by Bronchoalveolar Lavage Cells Harvested from Patients With or Without Chronic Obstructive Pulmonary Diseases" Pharmacol 1999;59: pp. 135-141.
Gibbs, et al., "Ambroxol inhibits the release of histamine, leukotrienes and cytokines from human leukocytes and mast cells" Inflamm. Res. 48 (1999), pp. 86-93.
Jablonka, et al., "The influence of Ambroxol on peroxidative processes in lung and plasma in dogs after pulmonectomy" Archivum Veterinarium Polonicum 32, 1-2, 1992, pp. 57-66.
Pawlak, et al., "Thiol Repletion Prevents Venous Thrombosis in Rats by Nitric Oxide/Prostacyclin-Dependent Mechanism: Relation to the Antithrombotic Action of Captopril" Journal of Cardiovascular Pharmacology, 36, 2000, pp. 503-509.
Djordjevic, et al., "Changes of lipid peroxides and antioxidative factors levels in blood of patients treated with ACE inhibitors" Clinical Nephrology, vol. 47 No. 4—1997. pp. 243-247.
De Cavanagh, et al., "Enalapril and captopril enhance glutathione-dependent antioxidant defenses in mouse tissues" Am. J. Physiol. Regulatory Integrative Comp. Physiol. 278, 2000, pp. R572-R577.
English Translation of International Preliminary Examination Report of PCT/DE02/01991, dated Sep. 2, 2003.
International Search Report of PCT/DE02/01991, dated Oct. 17, 2002.
International Preliminary Examination Report of PCT/DE02/01991, dated Sep. 2, 2003.
Han, et al., "α-Lipoic Acid Increases Intracellular Glutathione in a Human T-lymphocyte Jurkat Cell Line" Biochemical and Biophysical Research Communications, vol. 207, No. 1, Feb. 6, 1995, pp. 258-264, Berkeley, CA U.S.A., XP-000887357.
Varga, et al., "Mechanism of Allergic Cross-Reaction-I. Multispecific Binding of Ligands to a Mouse Monoclonal Anti-DNP IgE Antibody" Molecular Immunology, vol. 28, No. 6, pp. 641-654, 1991, Great Britain.
Rossi, et al.; *Thiol Groups In Proteins As Endogenous Reductants To Determine Glutathione-Protein Mixed Disulphides in Biological Systems*; Biochimica et Biophysica Acta 1243 (1995) pp. 230-238.
Schafer, et al; *Redox Environment Of The Cell As Viewed Through The Redox State Of The Glutathione Disulfide/Glutathione Couple*; Free Radical Biology & Medicine, vol. 30, No. 11, pp. 1191-1212, © 2001.
Tager, et al.; *Evidence Of A Defective Thiol Status Of Alveolar Macrophages From COPD Patients And Smokers*; Free Radical Biology & Medicine, vol. 29, No. 11, pp. 1160-1165, © 2000.
Bast, et al.' *α-Lipoic Acid and N-Acetylcysteine: New Concepts for Old Drugs*; Antioxyd. Health Des. 1995, pp. 409-425.

* cited by examiner

USE OF A MEDICAMENT CONTAINING AN EFFECTOR OF THE GLUTATHIONE METABOLISM TOGETHER WITH α-LIPOIC ACID IN KIDNEY REPLACEMENT THERAPY

CROSS-REFERENCE TO RELATED APPLICATION

This application is a National Phase Patent Application of International Application Number PCT/DE02/01991, filed on May 24, 2002, which claims priority of German Patent Application Number 101 25 883.6, filed on May 28, 2001.

BACKGROUND

The fine regulation of the thiol-disulfide status is one of the most important basic requirements of biological metabolic powers. The central regulation element within this system is the tripeptide glutathione, which reaches relatively high concentrations (up to 10 mM) intracellularly in reduced form. In addition to glutathione, proteins bearing thiol groups intracellularly and in particular in cell membrane-bound form are further important units of the thiol-disulfide status of each cell.

The metabolism of the disulfide cleavage and thiol group formation regulated by various enzyme classes is in its entirety indispensable for every normal cell function due to the variety of its biological functions, inter alia in cellular growth and differentiation processes including programmed cell death and cell protection and detoxification mechanisms. Disturbances in this system and changes in the concentration of thiols lead to serious cellular functional disorders, which only remain locally restricted in the isolated case, but as a rule adversely affect the entire organism.

It was possible to demonstrate the involvement of a disturbed thiol-disulfide status in acute and chronic disorders in a large number of investigations.

Thus, for example, marked changes in the thiol metabolism were detected in certain nerve cells in neurodegenerative disorders such as Parkinson's disease (Brain Res Rev 1997; 25:335-358). There are clear indications that as a result of this metabolic disturbance an increased death of the nerve cells substantially responsible for the symptomatology of the disorder occurs in functionally impaired areas of the brain, the basal ganglia (Ann Neurol 1994; 36:348-355).

Decreased glutathione levels or a decreased intracellular glutathione content was furthermore found in the course of vascular disorders and their sequelae—arteriosclerosis and cardiac infarct—in the endothelial cells lining the vascular inner wall (Med Sci Res 1998; 26:105-106).

Pulmonary disorders which are accompanied by a turnover of the lung tissue are regularly connected with a glutathione deficit in the tissue. In such pulmonary fibrosis, the degree of severity of the disorder proceeds in parallel to the thiol loss (Clin Chim Acta 1997; 265:113-119). Severe inflammatory pulmonary disorders, investigated in the example of adult acute respiratory distress syndrome, are accompanied by a dysregulation of the thiol metabolism of the inflammatory cells (granulocytes) involved (Chest 1996; 109:163-166).

Immunocompetent defense cells of the bronchial system (alveolar macrophages) of smokers and patients with chronic obstructive airways diseases exhibit, according to our own investigations, a severe cellular thiol deficit. The degree of the disturbance of the cellular thiol status in this case correlates directly with restrictions of the lung function (Free Radic Biol Med 2000; 29:1160-1165).

In recent years, increased references to a damaged thiol metabolism have been found in chronic kidney diseases (Ren Fail 1998; 20:117-124), anemia (Br J Haematol 1995; 91:811-819), immature newborn children (Pediatr Pulmonol 1995; 20:160-166), noise-related hearing loss (Brain Res 1998; 784:82-90), inflammatory intestinal disorders (Gut 1998; 42:485-492) and in diabetes mellitus (Metabolism: Clinical and Experimental 1998; 47(8):993-997).

Extensive investigations on the importance of the glutathione metabolism in virus infections demonstrated both a relatively poor prognosis of thiol-deficient cells, based on a damaged cellular defense, and an antiviral function of the glutathione inhibiting virus replication (Proc Natl Acad Sci USA 1997; 94:1967-1972). The cellular human immune system, consisting of the white blood cells granulocytes, lymphocytes and monocytes is a system reacting particularly sensitively to a disturbance in the thiol metabolism.

Minimal changes, in particular losses of cellular glutathione, can induce a cascade-like program for the self-destruction of the cell, programmed cell death (apoptosis) (FASEB J 1998; 12:479-486). The thiol-disulfide metabolism acts here as a central control member of an intact immune system, without which the organism would not be viable.

Our own investigations showed that in particular under the conditions of a high-grade restricted kidney function and kidney replacement therapy necessary as a result in the form of hemodialysis or peritoneal dialysis, the cellular thiol-disulfide metabolism is severely disturbed. This disturbance results, inter alia, in an extensive loss of normal cell functions, such as the phagocytic ability of peritoneal macrophages or the activatability of lymphocytes. In these patients, in addition to the existing local immune deficit, which is characterized by frequent infections of the abdominal cavity, a markedly decreased immunological defense with increased general susceptibility to infection are regularly found. Functional disturbances and a decreased activatability of the lymphocytes and macrophages, and imbalances of the immuno-regulatory cytokines are in particular described here (Immunobiol 1999; 200:62-76).

The correction of a disturbed thiol metabolism thus attains fundamental importance as a basic therapy in the treatment of a large number of disorders of different origin, but in particular under the conditions of a necessary kidney replacement therapy.

α-Lipoic acid is up to now being employed with relative success as a neuroprotective substance for the treatment of neurotoxically related paresthesias in diabetic polyneuropathy (Diabetologica 1995; 38:1425-1433, Diabetes Res Clin Pract 1995; 29:19-26, Diab Care 1999; 22:1296-1301, Drug Metab Rev 1997; 29:1025-1054, DE 43 43 592 C2). The use of α-lipoic acid in further neuronal disturbances including tinnitus and sudden deafness is moreover known from DE 44 47 599 C2 and EP 0 530 446 B1.

The cytoprotective mechanism of action is based here, in addition to the influencing of the sugar-dependent protein modification (protein glycosylation) and a decrease in the neurotoxic ketone body genesis, finally on the antioxidative function of the α-lipoic acid and its metabolites (Free Radic Biol Med 1995; 19:227-250).

This cell protection function was particularly investigated under the aspect of the prevention of the oxidative turnover of essential unsaturated fatty acids. Such an inhibition of the lipid peroxidation is, in addition to the use of α-lipoic acid as a neuroprotective, the basis for an application as a hepatoprotective medicament in various intoxications and liver disorders (Biochemistry 1998; 37:1357-1364).

Moreover, it was possible to show that α-lipoic acid inhibits the replication of the HI virus at different stages of development and thus could counteract progression of the AIDS disease. It was only possible, however, to transfer the results of these laboratory experiments restrictedly to clinical studies (FEBS-Lett 1996; 394:9-13). The same applies for the demonstration of an antiinflammatory function of the substance for the insulin-producing islet cells of the pancreas (Agents Actions 1993; 38:60-65).

In EP 0 812 590 A2 and EP 0 427 247 B1, the use of α-lipoic acid as a cytoprotective, analgesic and as a medicament in inflammatory diseases is disclosed.

The antioxidative properties of α-lipoic acid are based, in addition to the ability to form chelates with metal ions and directly to eliminate radicals, in particular on the function as a strong reductant. In order to carry out this reaction intracellularly, α-lipoic acid itself must be present in reduced form, as dihydrolipoic acid. The conversion of (disulfidic) α-lipoic acid by means of reduction to the dithiol form of dihydrolipoic acid uses, for its part, reducing equivalents, this process being catalyzed, inter alia, by the enzyme glutathione reductase (Gen Pharmacol 1997; 29:315-331). This is obviously the cause of the hitherto unsatisfactory action of the substance with respect to the thiol restitution.

DE 44 20 102 A1 describes a pharmaceutical combination of α-lipoic acid and cardiovascular-active substances, in particular an organic nitrate, a calcium antagonist, ACE inhibitor or oxyfedrine. The pharmaceutical combination should be employed for the treatment of cardiovascular diseases and diabetes-related diseases.

Ambroxole, i.e. trans-4-(2-amino-3,5-dibromobenzyl-amino)-cyclohexane hydrochloride is employed as a mucolytic medicament in various administration forms in lung and bronchial diseases (WO 96 33704, GB 2239242, WO 01 05378). Moreover, the use in hyperuricemia is known from DE 35 30 761. The action of ambroxole as a mucolytic is based both on a stimulation of the surfactant production of the bronchial cells and in particular on the ability to eliminate free radicals (Respir Med 1998; 92:609-23). This antioxidative activity of the substance based thereon was mainly demonstrated on pulmonary cells (Pharmacol 1999; 59: 135-141) but also in the context of inflammatory mechanisms (Inflamm Res 1999; 48:86-93). Furthermore, it is known that in vitro regulatory enzymes of the glutathione metabolism are directly influenced and per-oxidative processes are inhibited by the addition of ambroxole in high doses, and peroxidative processes are inhibited (Arch Vet Pol 1992; 32:57-66).

Angiotensin-converting enzyme inhibitors (ACE inhibitors) are employed with great success in the treatment of a wide range of cardiovascular diseases. The cause of the hypotensive action utilized here is based on the inhibition of the conversion of angiotensin I to angiotensin II. Moreover, ACE inhibitors were also described as effectors of the glutathione metabolism. In addition to investigations on relevant effects in cardiovascular and vascular disorders (J Cardiovasc Pharmacol 2000; 36:503-509) general regulation principles were investigated (Clin Nephrol 1997; 47:243-247). The actions of ACE inhibitors bearing SH groups, such as, for example, captopril (1-[(2S)-3-mercapto-2-methylpropionyl]-L-proline) from SH-free ACE inhibitors such as, for example, enalapril (1-{N—[(S)-1-ethoxycarbonyl-3-phenyl-propyl]-L-alanyl}-L-proline) are to be distinguished here. The former react directly as radical scavengers antioxidatively while SH-free ACE inhibitors are primarily not able to do this. Common to both groups is the influencing of the glutathione redox cycle via the regulation of the glutathione reductase and glutathione peroxidase, and furthermore superoxide dismutase (Am J Physiol Regulatory Integrative Comp. Physiol. 2000; 278:572-577).

Accordingly, there is a need to make available novel medicaments containing thiol-reactive substances for the improved stabilization of a damaged thiol-disulfide status, in particular in the case of renal insufficiency in kidney replacement therapy, and for the restitution of the functional losses caused thereby.

SUMMARY OF THE INVENTION

In one embodiment, the present invention is directed to a medicament comprising an effector of the glutathione metabolism together with α-lipoic acid, its salts and/or its prodrugs as a combination preparation for the simultaneous, separate or sequential treatment of a disturbance of the thiol-disulfide status in kidney replacement therapy, and syndromes in which a disturbance of the thiol-disulfide status of immune cells occurs, where as an effector ambroxole having the general formula

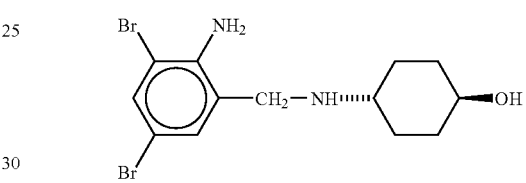

its salts and/or its prodrugs is used.

In another embodiment, the present invention is directed to the use of at least one effector of the glutathione metabolism together with α-lipoic acid, its salts and/or its prodrugs for the production of a medicament for the simultaneous, separate or sequential treatment of a disturbance of the thiol-disulfide status in kidney replacement therapy in the form of a hemo- or peritoneal dialysis process.

In still another embodiment, the present invention is directed to the use of at least one effector of the glutathione metabolism together with α-lipoic acid, its salts and/or its prodrugs for the production of a medicament for the simultaneous, separate or sequential treatment of a disturbance of the thiol-disulfide status in syndromes in which a disturbance of the thiol-disulfide status of immune cells occurs, in particular for simultaneous, separate or sequential immuno-modulatory, defense-increasing and/or anti-inflammatory treatment.

DETAILED DESCRIPTION OF THE INVENTION

Figure 1:
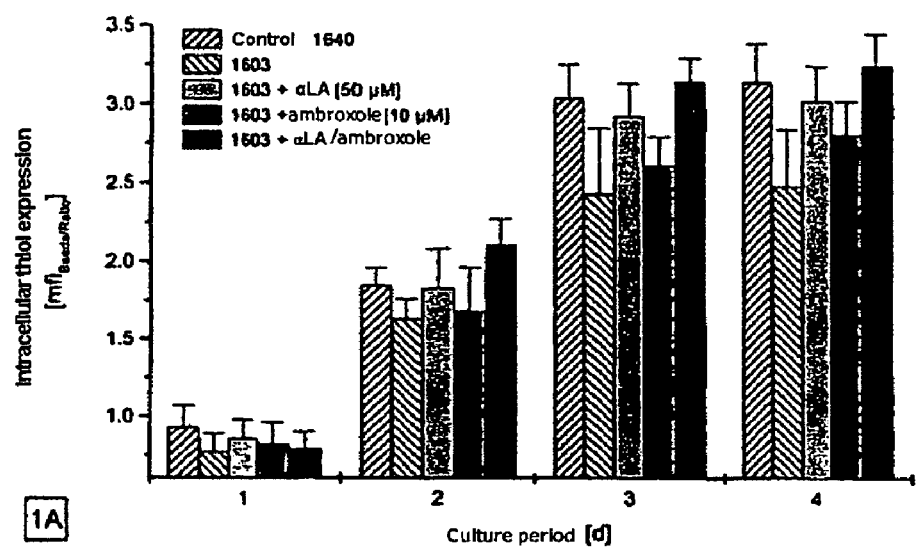
FIG. 1 is a graph showing the action of the combination of α-lipoic acid and ambroxole (FIG. 1a) and α-lipoic acid and enalapril (FIG. 1b) on the intracellular thiol expression of lymphocytes.
Figure 1:
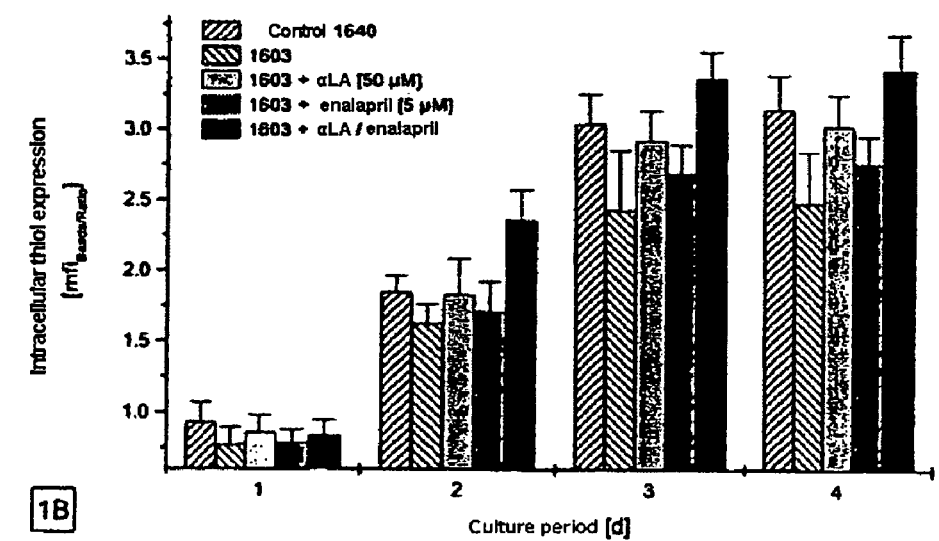

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, compositions and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

In one embodiment of the present invention, effectors of glutathione metabolism are employed in combination with α-lipoic acid, its salts and/or its prodrugs. Surprisingly, it was possible to show that by the administration of the combination of α-lipoic acid and an effector of the glutathione metabolism used according to the invention a normalization of the primarily decreased thiol status of immune cells took place. The thiol-stabilizing action of the combinations in this case exceeded that of the sole use of α-lipoic acid or of the respective effectors not only regularly, but on the contrary superadditive effects were also able to be detected. The restitution of the thiol status in this case covered both intracellular thiols and membrane-bound SH groups and is thus an expression of a complex biological regulation. This phenomenon is based on the fact that the effectors of the glutathione metabolism on the one hand eliminate intermediately resulting free radicals and on the other hand increase the availability of reducing equivalents for the conversion of the α-lipoic acid from disulfidic to reduced form and thus improve the synthesis-inducing action of the α-lipoic acid on the thiol-disulfide status.

Moreover, it was clear that a thiol-increasing action of the combination of effectors of the glutathione metabolism and α-lipoic acid only occurred in primarily thiol-deficient immune cells. Healthy immune cells which exhibited no alteration of the thiol-disulfide status did not react with a further increase in the SH concentration.

The restitution of the thiol status of the immune cells was accompanied by a normalization of functional parameters. This related in particular to the immunomodulatory effects in the context of the activatability of T lymphocytes.

Furthermore, it was possible to show that the combinations used according to the invention stabilized the thiol-disulfide status of further immune cells such as the peritoneal macrophages of dialysis-dependent patients. Before the treatment with α-lipoic acid/ambroxole or α-lipoic acid/ACE inhibitors, the peritoneal macrophages exhibited, in addition to a deficient thiol status, an almost complete loss of their phagocytic function and a severe disturbance of the differentiation and cytokine synthesis, which are described as causal for the high infection rates in these patients. These functional losses were able to be offset by the addition of the combinations named according to the invention.

This medicament is particularly suitable in kidney replacement therapy and further syndromes in which a disturbance of the thiol-disulfide status of the immune cells occurs. In this connection, the treatment can be carried out simultaneously, in separate formulations or alternatively sequentially.

The combination preparations used according to the invention can be administered in the customary pharmacological administration forms or as an instillate and also prophylactically and therapeutic-ally. The effective dose is to be determined here in a case-related manner. Preferably, in the case of human medicinal administration to the patient, it is between 30 and 1200 mg/d, particularly preferably between 200 and 600 mg/d.

In one variant, the effector of the glutathione metabolism used is ambroxole of the general formula I,

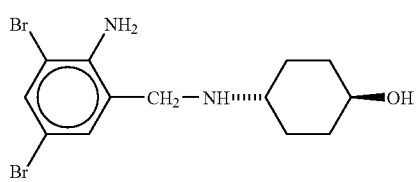

its salts and/or its prodrug. The dose of ambroxole for human medical application is in this case preferably between 7.5 and 90 mg/d, particularly preferably between 60 and 75 mg/d.

In a further variant, the effector of the glutathione metabolism used is an angiotensin-converting enzyme inhibitor (ACE inhibitor). Here, the preferred dose for human medicinal administration is between 0.2 and 20 mg/d.

ACE inhibitors which can be employed here are, for example, the following compounds:

A) 1-[(2S)-3-mercapto-2-methylpropionyl]-L-proline (Captopril) of the Formula II

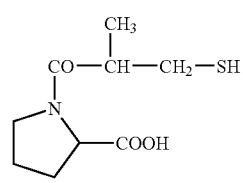

B) 1-{N—[(S)-1-ethoxycarbonyl-3-phenylpropyl]-L-alanyl}-L-proline (Enalapril) of the Formula III

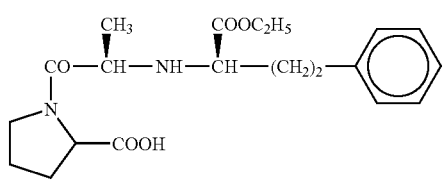

C) (2S,3aS,6aS)-1-{(S)—N—[(S)-1-ethoxycarbonyl-3-phenylpropyl]-alanyl}-octahydrocyclopenta[b]-pyrrole-2-carboxylic Acid (Ramipril) of the Formula IV

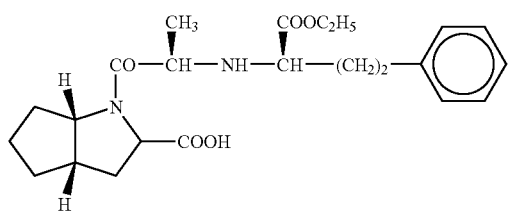

IV

The medicaments can be administered orally or alternatively parenterally here.

Additionally, the medicaments can contain customary additives. These include, for example, aqueous solvents, stabilizers, suspending, dispersing and wetting agents.

The medicament can be prepared in any desired formulation. These include, for example, solutions, granules, powders, emulsions, tablets and/or film-coated tablets.

According to the invention, an effector of the glutathione metabolism is used together with α-lipoic acid, its salt and/or its prodrugs for the production of a medicament for the treatment of a disturbance of the thiol-disulfide status of immune cells in kidney replacement therapy.

Likewise, an effector of the glutathione metabolism can be employed together with α-lipoic acid, its salt and/or its prodrugs for the production of a medicament for immunomodulatory, defense-increasing and/or anti-inflammatory treatment.

The components of the combination preparation can be present here either in a single formulation or in separate formulations.

The use according to the invention of the combination of α-lipoic acid and effectors of the glutathione metabolism is described in greater detail with the aid of the following examples and figures.

EXAMPLE 1

Influence on the Cellular Thiol Status of Peripheral Human Immune Cells

Peripheral immune cells of healthy donors (n=9) were isolated from the peripheral blood by means of density gradient centrifugation. Lymphocytes having a donor-dependent relative proportion of about 90% in this case normally represent the main fraction of the resulting total population of mononuclear cells. 10% of the mononuclear cells are represented by monocytes.

The mononuclear cells obtained were taken up in special cell culture media and incubated in a gas incubator at 37° C., a relative humidity of 98% and 5% relative air-$CO_2$ content. The metabolism of the primarily resting immune cells was activated by means of mitogenic stimulation (0.5 μg/ml of phytohemagglutinin). In order to test the influence of the combinations used according to the invention on the thiol status of thiol-deficient immune cells, these were artificially thiol-depleted. This was carried out by culturing in thiol-deficient media (RPMI 1603) according to tested procedures.

Comparison cultures using whole media (RPMI 1640) served for the definition of the best possible normal value under culture conditions.

The determination of the intercellular thiol content at the individual cell level was carried out using 5-chloromethylfluorescein diacetate (CMFDA) in flow cytofluorimetry.

Primarily nonfluorogenic CMFDA is in this case passively taken up by the cell. Binding to cytoplasmic thiol groups takes place via the chloromethyl radical. After removal of the acetate radicals by nonspecific cellular esterases, this, now cell membrane-impermeable complex becomes fluorogenic at an excitation wavelength $\lambda_{ex}$=490 nm with an emission wavelength $\lambda_{em}$=520 nm. The mean fluorescence intensity of the sample (10,000 cells) is directly proportional to the concentration of the intracellular thiol groups.

The expression of membrane-bound thiol groups was likewise determined by flow cytofluorimetry. In this connection, chloromethyltetramethylrhodamine (CMTMR) was employed as a thiol conjugate under the conditions of a blocked membrane potential and of an inhibited diffusion capacity of the cells. The fluorescence intensity of the bound fluorochrome molecules on the cell membrane is in this case in turn proportional to the amount of the thiol groups on the cell surface.

In FIG. 1, the action of the combination of α-lipoic acid and ambroxole (FIG. 1a) and α-lipoic acid and enalapril (FIG. 1b) on the intracellular thiol expression of lymphocytes is shown. Table 1 shows the results of the combination of α-lipoic acid and captopril. The data are shown as the ratio of the cellular fluorescence intensity for calibration particles (beads) in each case analyzed in parallel. The active compound concentration of the respective combination is identical to the concentrations of the individual components.

TABLE 1

| | intracellular thiol expression [mfi$_{Beads/Ratio}$] | | | |
|---|---|---|---|---|
| culture period [d] | control | α-lipoic acid [50 μM] | captopril [10 μM] | α-lipoic acid + captopril |
| 0 | 2.88 ± 0.20 | 2.88 ± 0.20 | 2.88 ± 0.20 | 2.88 ± 0.20 |
| 1 | 2.31 ± 0.20 | 2.81 ± 0.23 | 2.80 ± 0.21 | 2.89 ± 0.31 |
| 2 | 1.98 ± 0.16 | 2.76 ± 0.50 | 2.76 ± 0.22 | 2.92 ± 0.32 |
| 3 | 1.63 ± 0.15 | 2.63 ± 0.60 | 2.49 ± 0.26 | 2.88 ± 0.41 |
| 4 | 1.30 ± 0.16 | 2.41 ± 0.40 | 2.21 ± 0.36 | 2.91 ± 0.39 |
| 6 | 1.10 ± 0.13 | 2.23 ± 0.50 | 1.83 ± 0.33 | 2.93 ± 0.35 |
| 8 | 0.95 ± 0.10 | 2.02 ± 0.30 | 1.02 ± 0.39 | 2.93 ± 0.41 |
| 10 | 0.81 ± 0.10 | 1.89 ± 0.30 | 0.91 ± 0.46 | 2.90 ± 0.45 |
| 12 | 0.69 ± 0.10 | 1.86 ± 0.68 | 0.76 ± 0.49 | 2.88 ± 0.49 |
| 14 | 0.65 ± 0.08 | 1.83 ± 0.60 | 0.75 ± 0.56 | 2.86 ± 0.47 |

Peripheral immune cells were cultured over a period of 4 days under normal (control 1640) or thiol-deficient conditions (1603) for the induction of a 10-20% strength thiol reduction. As shown in 1a, the addition of ambroxole in combination with α-lipoic acid beginning after a treatment period of 48 hours resulted in a complete equalization of the intracellular thiol deficit. Using the combination of α-lipoic acid and the SH-free ACE inhibitor enalapril, and the SH-bearing ACE inhibitor captopril, these effects were additionally quantitatively reinforced, and detectable in the time kinetics as early as after 24 hours. Neither by α-lipoic acid alone nor by the individual application of the effectors was a complete equalization of the thiol deficit possible.

Figure 2:
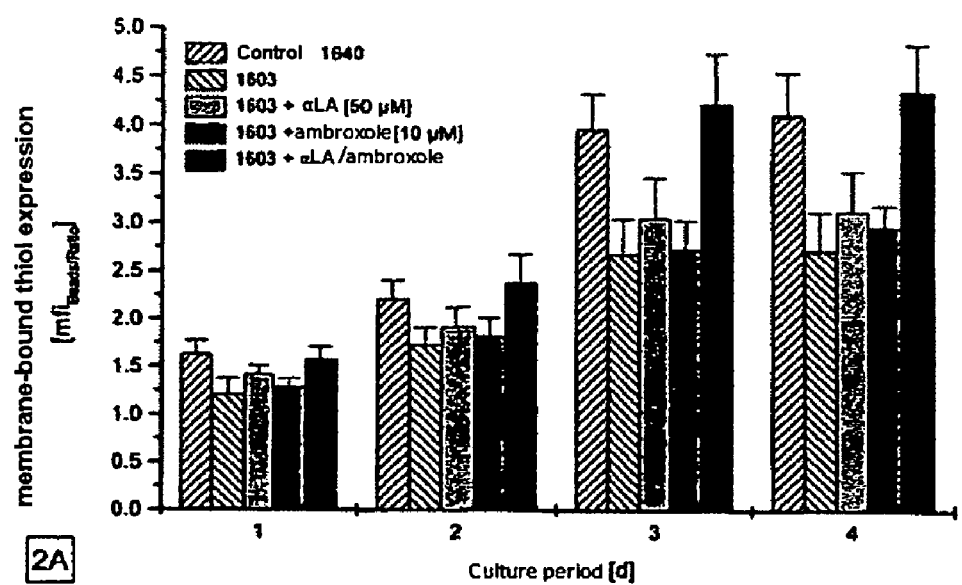
FIG. 2 is a graph showing the action of the combination of α-lipoic acid and ambroxole (FIG. 2a) and α-lipoic acid and enalapril (FIG. 2b) on the expression of cell membrane-bound thiols.
Figure 2:
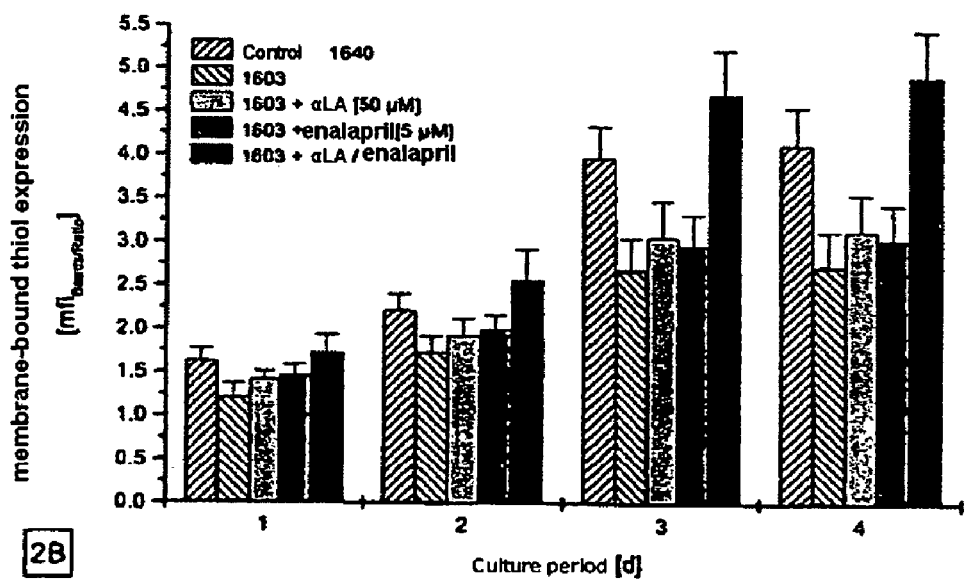

The results obtained using this experimental batch for the influence of the combinations named according to the invention on the expression of cell membrane-bound thiols are presented in FIG. 2 for the combination of α-lipoic acid and ambroxole (FIG. 2a), and α-lipoic acid and enalapril (FIG. 2b); table 2 shows the results of the combination of α-lipoic acid and captopril.

TABLE 2

Membrane-bound thiol expression [mfi$_{Beads/Ratio}$]

| culture period [d] | control | α-lipoic acid [50 µM] | captopril [10 µM] | α-lipoic acid + captopril |
|---|---|---|---|---|
| 0  | 2.37 ± 0.45 | 2.37 ± 0.45 | 2.37 ± 0.45 | 2.37 ± 0.39 |
| 1  | 2.79 ± 0.50 | 2.65 ± 0.39 | 2.63 ± 0.39 | 2.38 ± 0.38 |
| 2  | 2.35 ± 0.45 | 2.43 ± 0.52 | 2.54 ± 0.41 | 2.42 ± 0.41 |
| 3  | 1.98 ± 0.43 | 2.31 ± 0.36 | 2.52 ± 0.38 | 2.49 ± 0.46 |
| 4  | 1.63 ± 0.43 | 2.26 ± 0.20 | 2.50 ± 0.41 | 2.39 ± 0.52 |
| 6  | 1.10 ± 0.46 | 2.19 ± 0.13 | 2.46 ± 0.50 | 2.40 ± 0.50 |
| 8  | 0.98 ± 0.31 | 1.93 ± 0.20 | 2.01 ± 0.39 | 2.40 ± 0.53 |
| 10 | 0.96 ± 0.32 | 1.63 ± 0.16 | 1.68 ± 0.29 | 2.36 ± 0.52 |
| 12 | 0.95 ± 0.33 | 1.32 ± 0.21 | 1.02 ± 0.51 | 2.38 ± 0.49 |
| 14 | 0.98 ± 0.33 | 1.34 ± 0.20 | 0.99 ± 0.46 | 2.36 ± 0.55 |

Under the treatment with the combination α-lipoic acid and ambroxole, again, beginning after 48 hours, a significant improvement in the membrane-bound thiol expression occurred. It was particularly obvious here that the administration of the individual substances did not show a significant influence at any point in time. The addition of the combination of α-lipoic acid and the respective ACE inhibitors resulted both in the case of enalapril and in the case of captopril in a superadditive effect.

EXAMPLE 2

Influence on the Cellular Activation Status of Peripheral Human T Lymphocytes

Figure 3:
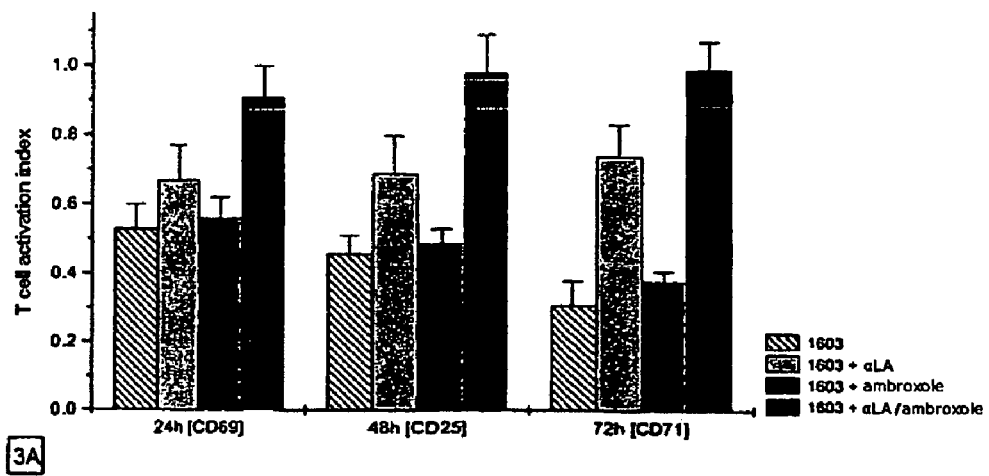
FIG. 3 is a graph showing the action of the combination of α-lipoic acid and ambroxole (FIG. 3a), and α-lipoic acid and enalapril (FIG. 3b) on the activation index of T lymphocytes.
Figure 3:
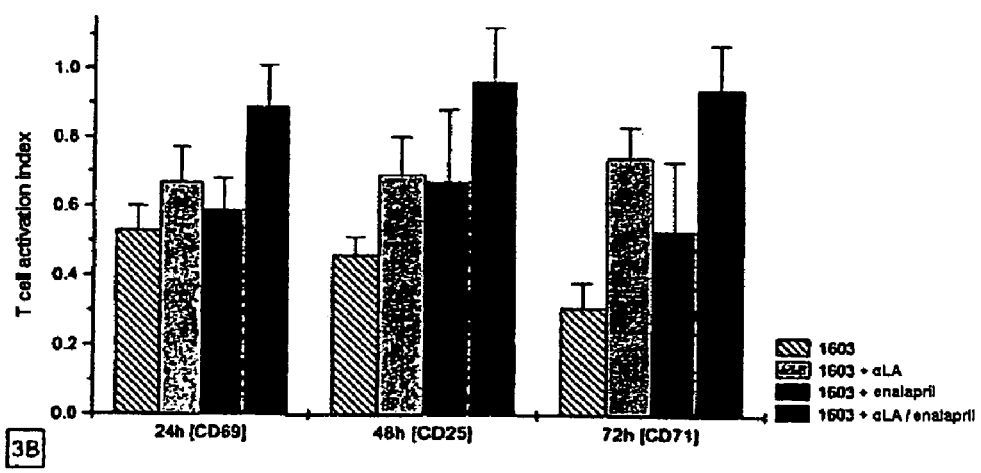

In the culture batch described under example 1, human T lymphocytes were stimulated with 1.0 µg/ml of phyto-hemagglutinin. Within a culture period of 72 hours, specific markers of the cellular activation were demonstrated quantitatively cytofluorometrically by detection by means of monoclonal antibodies. The influence of the combinations used according to the invention on the activation markers CD69 (early activation antigen), CD25 (intermediate activation antigen) and CD71 (late activation antigen) of T lymphocytes was investigated. In FIG. 3, the action of the combination of α-lipoic acid and ambroxole (FIG. 3a), and α-lipoic acid and enalapril (FIG. 3b) on the activation index of T lymphocytes is shown. Compared with normal T lymphocytes (activation index=1.0), in thiol-deficient cells a clear lowering of the activatability, confirming the cellular functional disorder, is to be noted. After addition of α-lipoic acid, the known effect of a slight improvement in the cellular activatability occurs, which, however, in no case eliminates the significant difference from the normal control group. Ambroxole shows no influence on one of the three activation markers; the ACE inhibitor enalapril is only equivalent in the case of the effectuation of the CD25 antigen of the α-lipoic acid. In contrast, both in the case of the combined administration of α-lipoic acid and ambroxole, and of α-lipoic acid and enalapril, a raising of the T cell activation index into the normal range was detectable. This effect was observed in the case of early, intermediate and late activation markers. It can thus be concluded that the normalization of the cellular thiol status mediated by the combined use of α-lipoic acid and the respective effectors of the glutathione metabolism is accompanied by a restitution of the cellular functionality.

EXAMPLE 3

Influence on the Cellular Thiol Status of Peritoneal Macrophages in Kidney Replacement Therapy Peritoneal macrophages were isolated from the effluate of the peritoneal dialysis of high-grade renally insufficient patients, taken up in cell culture medium and incubated in a gas incubator at 37° C., a relative humidity of 98% and 7.5% relative air-$CO_2$ content. In order to test the influence of the combinations used according to the invention on the thiol status of the peritoneal macrophages, in each case a fraction was treated with α-lipoic acid, the effector of the glutathione metabolism ambroxole or the ACE inhibitor enalapril or with the combination of α-lipoic acid/ambroxole or α-lipoic acid/enalapril, while in each case a further fraction was used as an untreated control.

The determination of the cellular thiol status was carried out by means of the measuring method described under 1. The membrane expression of thiols was determined by means of the mean fluorescence intensity (mfi) of the sample (3000 cells/measurement) after coupling to a chloromethylfluorochrome derivative.

Figure 4:
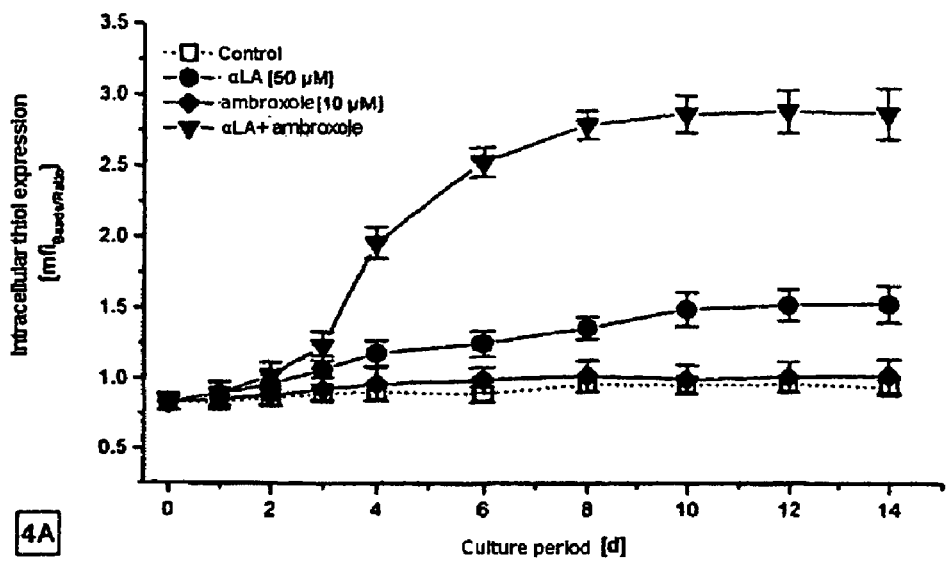
FIG. 4 is a graph showing the effect of the combination of α-lipoic acid and ambroxole (FIG. 4a), and α-lipoic acid and enalapril (FIG. 4b) on time kinetics over 14 days (n=12).
Figure 4:
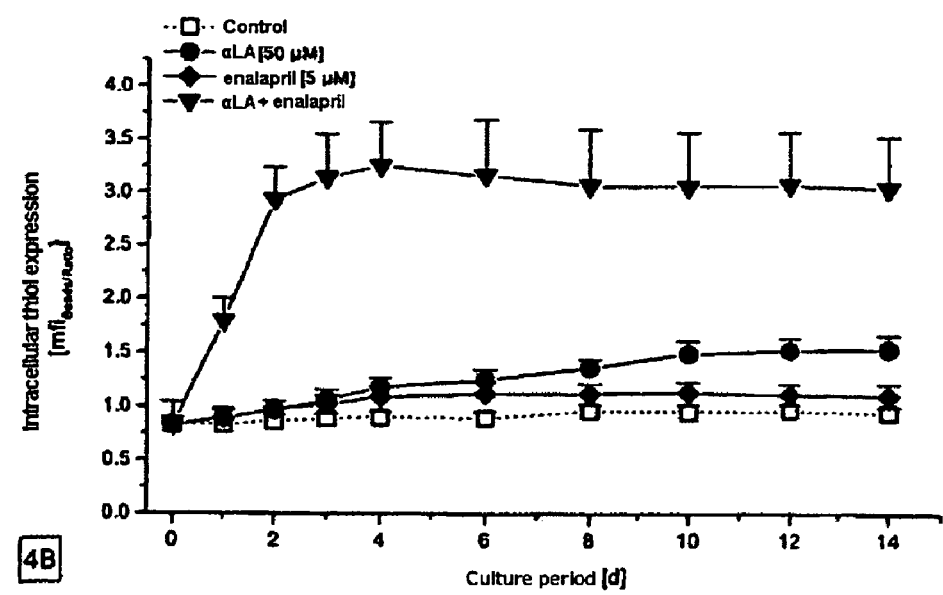

In FIG. 4, the effect of the combination of α-lipoic acid and ambroxole (FIG. 4a), and α-lipoic acid and enalapril (FIG. 4b) in the time kinetics over 14 days is shown (n=12).

With addition of the monosubstances, in turn only an increase in the cellular thiol expression using α-lipoic acid was to be observed, while ambroxole and the ACE inhibitor showed no effect. In contrast, with the combination of α-lipoic acid and ambroxole beginning after 72 hours a clear increase in the cellular thiol expression was detectable, which after a treatment period of 4 days reached a superadditive effect and after 8 days a maximum, which exceeded the starting or control data by threefold (FIG. 4a). The combination of α-lipoic acid and an ACE inhibitor (FIG. 4b) resulted in a similar, but again markedly shortened time kinetics. A maximum in the superadditive action was reached here as early as after a treatment period of 48-72 hours.

Figure 5:
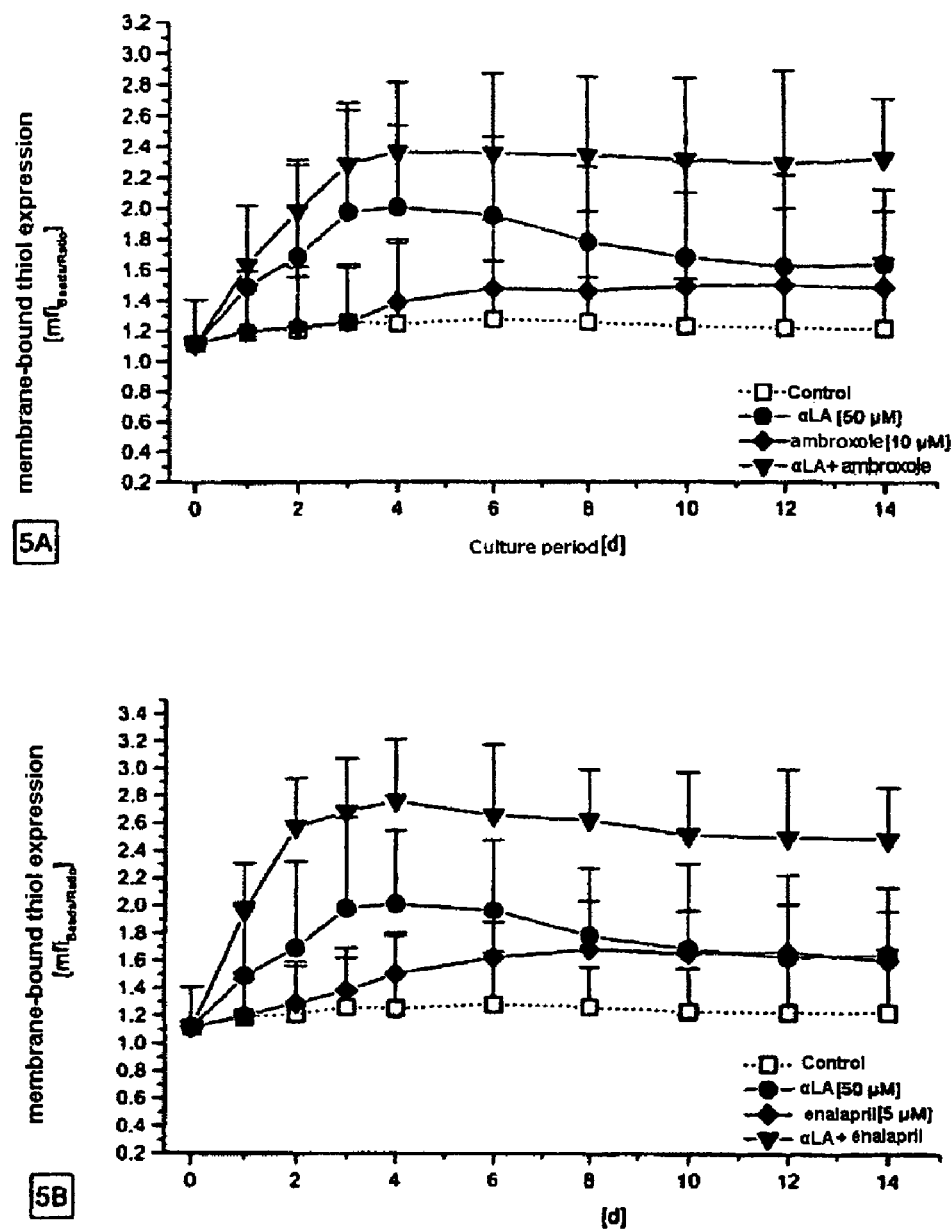
FIG. 5 is a graph showing the action of the combination of α-lipoic acid and ambroxole (FIG. 5a) and α-lipoic acid and enalapril (FIG. 5b) on the membrane-bound thiol expression of peritoneal macrophages.

In FIG. 5, the action of the combination of α-lipoic acid and enalapril (FIG. 5b) on the membrane-bound thiol expression of peritoneal macrophages in the experimental setup described above is presented. The membrane expression of thiols was determined by means of the mean fluorescence intensity (mfi) of the sample (3000 cells/measurement) after coupling to a chloro-methylfluorochrome derivative. In comparison with the results of the intracellular thiol expression, a very marked effect of the sole administration of α-lipoic acid is to be noted here, which, however, is cancelled out again after 4 days of treatment. In contrast to this, the combined administration of α-lipoic acid and ambroxole (FIG. 5a), or α-lipoic acid and an ACE inhibitor (FIG. 5b) brings about both a primarily more marked and also superadditive increase, which is stable beyond the observation time period, in the membrane-bound thiol expression.

EXAMPLE 4

Influence on the Phagocytic Ability of Peritoneal Macrophages

In order to make possible a characterization of the peritoneal macrophages with respect to their original functions, the phagocytic ability was selected as a measurement variable.

Peritoneal macrophages were isolated analogously to the procedure described under example 3 and cultured ex vivo. The determination of the phagocytic power was carried out by means of a cytofluorometric test at the individual cell level. In this test, the macrophages were cocultured with opsonized and fluorochrome-labelled bacteria. The amount of bacteria taken up in a defined time period was recorded quantitatively by means of the fluorescence intensity in the macrophages and was regarded as a measure of their phagocytic capacity.

The influence of the combinations used according to the invention on the phagocytic ability of the peritoneal macrophages after a treatment period of 6 days is presented in Table 3.

TABLE 3

|  | Phagocytosis rate [mfi/10,000 cells] |
|---|---|
| Control | 371 ± 39 |
| α-lipoic acid [50 μM] | 687 ± 59 |
| Ambroxole [10 μM] | 501 ± 52 |
| α-lipoic acid + ambroxole | 1398 ± 286 ($p < 0.05$) |
| Enalapril [5 μM] | 567 ± 59 |
| α-lipoic acid + enalapril | 1698 ± 241 ($p < 0.05$) |
| Captopril [10 μM] | 653 ± 43 |
| α-lipoic acid + captopril | 1589 ± 176 ($p < 0.05$) |

After incubation with α-lipoic acid, ambroxole or enalapril, the phagocytosis rate was increased in relation to the untreated control by the factor 1.85 (α-lipoic acid), 1.35 (ambroxole) or 1.53 (enalapril). In contrast, it was possible using the combination of α-lipoic acid and ambroxole to achieve an increase in the phagocytosis rate by the factor 3.7, when using the combination of α-lipoic acid and an ACE inhibitor by the factor 4.6 (enalapril) or 4.3 (captopril).

Moreover, it was possible to demonstrate a direct correlation between the phagocytosis rate and the intracellular thiol content of the peritoneal macrophages for the combination of α-lipoic acid and ambroxole ($r=0.79$; $p<0.01$), α-lipoic acid and captopril ($r=0.86$; $p<0.01$), and α-lipoic acid and enalapril ($r=0.82$; $p<0.01$).

EXAMPLE 5

Influence on the Degree of Differentiation and Activation and the Cytokine Synthesis of Peritoneal Macrophages Peritoneal macrophages were isolated from patients under kidney replacement therapy according to the processes described under example 3 and cultured in the presence of the combinations of α-lipoic acid and effectors of the glutathione metabolism named according to the invention. After incubation for 6 days, the degree of differentiation of the peritoneal macrophages was determined cytofluorometrically by means of the expression of the cell surface antigens CD15 and CD11c, and the degree of cellular activation by means of the coexpression of the activation antigens CD69 on CD15-positive cells and CD71 on CD11c-positive cells.

The results are summarized in Table 4.

TABLE 4

|  | CD15 | CD11c | CD15/69 | CD11c/71 |
|---|---|---|---|---|
| Control | 1.0 | 1.0 | 1.0 | 1.0 |
| α-lipoic acid [50 μM] | 1.18 ± 0.16 | 1.21 ± 0.11 | 1.09 ± 0.08 | 1.08 ± 0.09 |
| Ambroxole [10 μM] | 0.98 ± 0.13 | 1.01 ± 0.09 | 0.98 ± 0.11 | 0.96 ± 0.1 |
| α-lipoic acid + ambroxole | 1.29 ± 0.21 | 1.65 ± 0.21 | 1.49 ± 0.13 | 1.83 ± 0.14 |
| Enalapril [5 μM] | 1.21 ± 0.22 | 1.23 ± 0.22 | 1.19 ± 0.12 | 1.10 ± 0.14 |
| α-lipoic acid + enalapril | 2.12 ± 0.16 ($p < 0.05$) | 1.99 ± 0.15 ($p < 0.05$) | 1.69 ± 0.2 | 1.58 ± 0.12 |
| Captopril [10 μM] | 1.19 ± 0.14 | 1.26 ± 0.24 | 1.69 ± 0.21 | 1.52 ± 0.16 |
| α-lipoic acid + captopril | 2.25 ± 0.2 ($p < 0.05$) | 2.63 ± 0.23 ($p < 0.05$) | 1.74 ± 0.19 | 1.61 ± 0.18 |

It was possible to show that the expression of the maturity markers CD15 and CD11c increased markedly using the combination of α-lipoic acid and ambroxole, and significantly using the combination α-lipoic acid and ACE inhibitor. Moreover, a marked increase in the activation antigens CD69 and CD71 on the respective cell populations was detectable. The administration of the monosubstances had no influence or only a marginal influence on the degree of differentiation and activation of the peritoneal macrophages.

In parallel to this, in this experimental batch the cell culture supernatants were recovered and the cytokines interleukin-6 (IL-6) and interleukin-1 receptor antagonist (IL-1ra) contained therein, synthesized and secreted by the peritoneal macrophages, were determined. The analysis was carried out using the enzyme immunoassay technique with standardized measuring systems and is presented in Table 5, which shows the effects of α-lipoic acid and effectors of the cellular glutathione metabolism on the cytokine synthesis of peritoneal macrophages after a treatment period of 6 days (n=10).

TABLE 5

|  | IL-6 [ng/$10^6$ cells] | IL-1ra [ng/$10^6$ cells] |
|---|---|---|
| Control | 53.1 ± 8.9 | 115.2 ± 23.4 |
| α-lipoic acid [50 μM] | 46.9 ± 6.7 | 119.8 ± 19.5 |
| Ambroxole [10 μM] | 51.8 ± 8.1 | 118.6 ± 21.3 |
| α-lipoic acid + ambroxole | 31.5 ± 9.2 ($p < 0.05$) | 126.8 ± 15.3 ($p < 0.05$) |
| Enalapril [5 μM] | 41.7 ± 7.3 | 121.1 ± 16.9 |
| α-lipoic acid + enalapril | 22.3 ± 8.1 ($p < 0.05$) | 139.8 ± 22.1 ($p < 0.05$) |
| Captopril [10 μM] | 42.9 ± 7.7 | 129.4 ± 25.1 |
| α-lipoic acid + captopril | 28.1 ± 6.1 ($p < 0.05$) | 143.5 ± 18.7 ($p < 0.05$) |

In the presence of the combination of α-lipoic acid and ambroxole, and the combination of α-lipoic acid and the different ACE inhibitors, a significant reduction of the IL-6 synthesis was detectable. This effect in turn clearly went beyond the sum of the decrease mediated by the monosubstances. The synthesis of IL-1ra was induced significantly under these conditions. Here too, a superadditive influence of the combination of α-lipoic acid and ambroxole or ACE inhibitors was to be noted.

EXAMPLE 6

Figure 6:
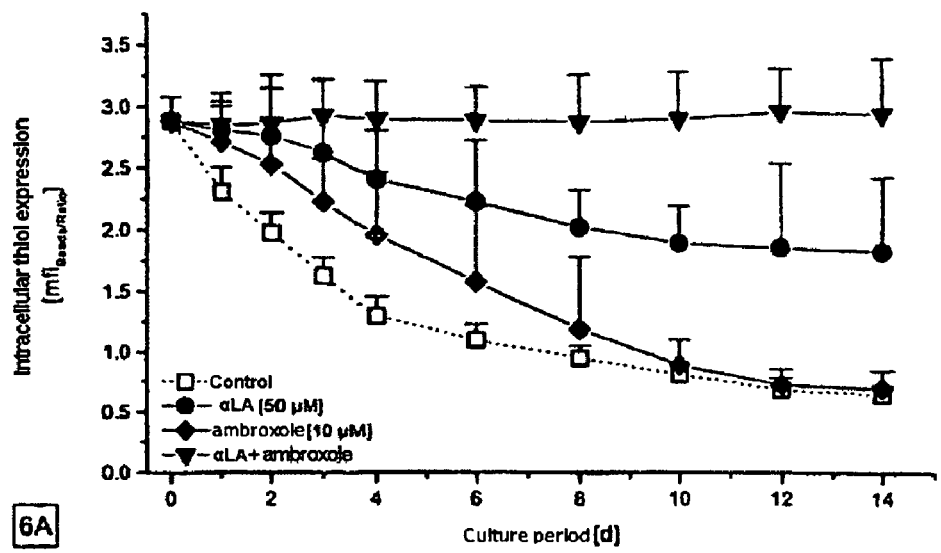
FIG. 6 is a graph showing the action of the combination of α-lipoic acid and ambroxole (FIG. 6a), and α-lipoic acid and enalapril (FIG. 6b) on the intracellular thiol expression of the peritoneal macrophages in the time kinetics.
Figure 6:
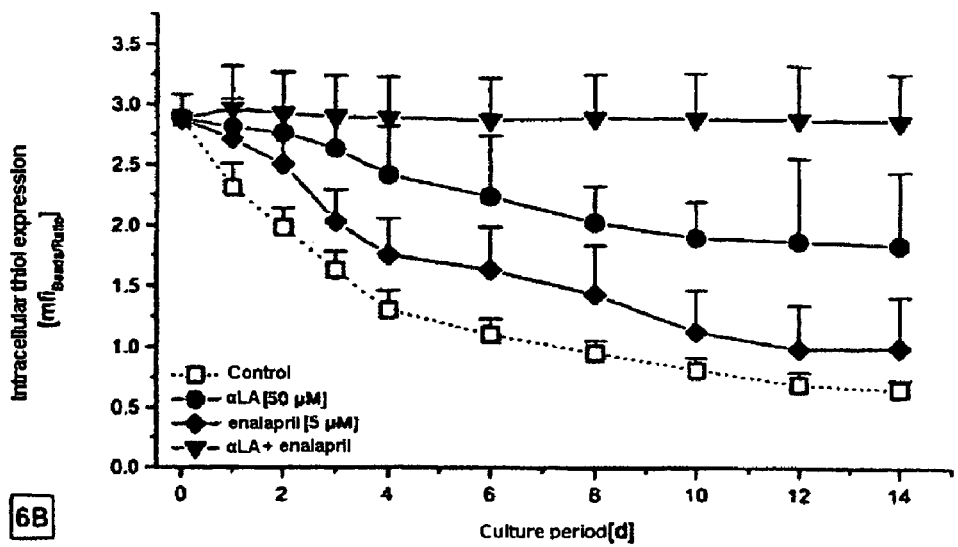

Influence on the Stability of the Thiol Restitution in Peritoneal Macrophages in the Dialysis Model The peritoneal macrophages described under example 3, which were thiol-restituted by means of the combinations used according to the invention, were removed from this test system after 6 days and cultured in a dialysis model over a period of 14 days. For this, the peritoneal macrophages were adapted to mobile collagen IV-coated matrices and brought into contact with conventional dialysis solution 3 times daily for 60 minutes each. This model served here for the induction of a combined hypoglycemic/osmotic stress. In FIG. 6, the action of the combination of α-lipoic acid and ambroxole (FIG. 6*a*), and α-lipoic acid and enalapril (FIG. 6*b*) on the intracellular thiol expression of the peritoneal macrophages in the time kinetics is presented. The membrane expression of thiols was determined by means of the mean fluorescence intensity (mfi) of the sample (3000 cells/measurement) after coupling to a chloro-methylfluorochrome derivative.

While in the case of the primary thiol-restituted controls, which were untreated in this dialysis model, within the first 4 days an almost linear fall of the intracellular thiol concentration was to be noted, and the combined addition of α-lipoic acid and ambroxole, and of α-lipoic acid and enalapril, resulted in a constant intracellular thiol status at the level of the primary restitution. Here too, a monoeffect is detectable in particular by α-lipoic acid, which, however, is only short-lasting and after about 4 days in the dialysis model shows only approximately 50% of the action of the combinations.

Figure 7:
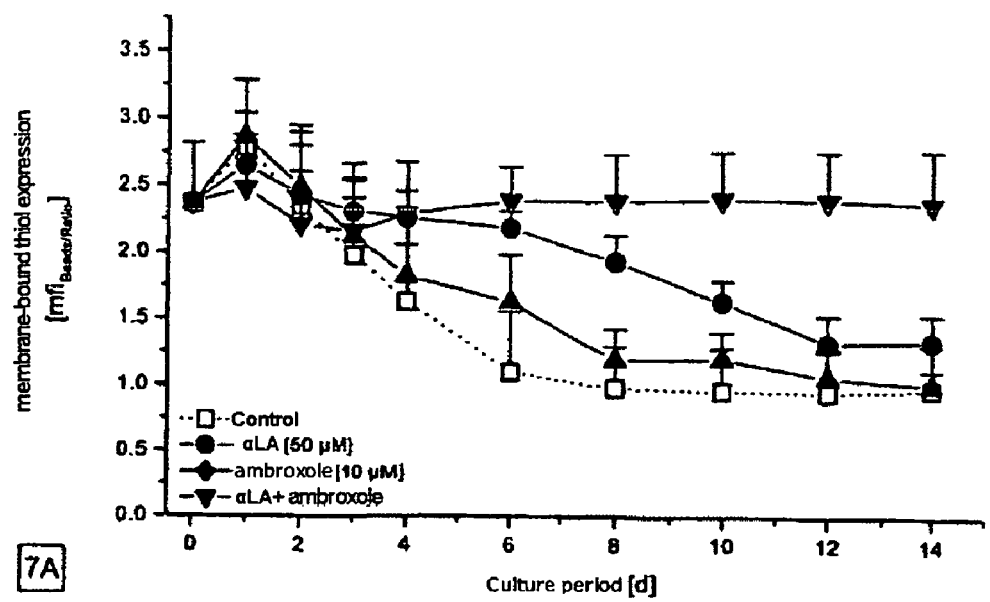
FIG. 7 is a graph showing the action of the combination of α-lipoic acid and ambroxole (FIG. 7a), and α-lipoic acid and enalapril (FIG. 7b) on the courses of the membrane-bound thiol expression.
Figure 7:
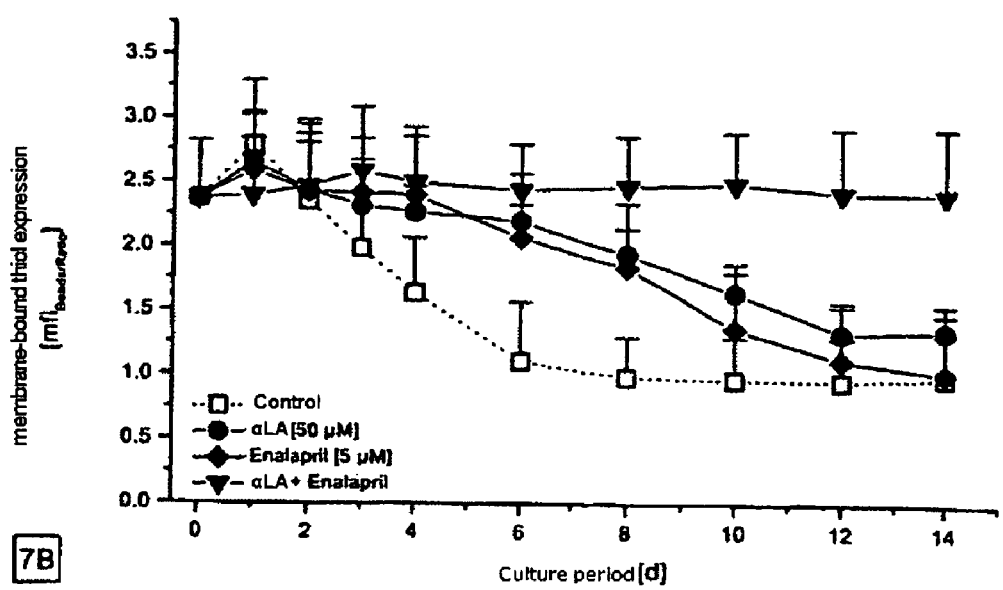

A similar picture suggests itself in the consideration of the courses of the membrane-bound thiol expression presented in FIG. 7. Again, the quantities obtained by the primary thiol restitution are kept constant by use of the combination of α-lipoic acid and ambroxole (FIG. 7*a*) or ACE inhibitors (FIG. 7*b*), while with addition of the monosubstances only intermediate α-lipoic acid) or marginal effects (ambroxole, enalapril) were observed.

All in all, these experiments make it clear that the administration of the combination of α-lipoic acid and the effectors of the glutathione metabolism ambroxole or ACE inhibitors stabilizes a primarily severely damaged thiol status in different cell systems. By means of this normalization, a restoration of central cellular immunoregulatory functions moreover occurs, which is not to be noted without such a treatment.

While this invention has been described in detail with reference to a certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention. In particular, it is to be understood that this invention is not limited to the particular methodology, protocols, constructs, and reagents described as such may vary, as will be appreciated by one of skill in the art. The scope of the invention is, therefore, indicated by the following claims rather than by the foregoing description. All changes, modifications, and variations coming within the meaning and range of equivalency of the claims are to be considered within their scope.

The invention claimed is:

1. A method for treating a disturbance of a patient's thiol-disulfide status in a patient undergoing kidney replacement therapy, comprising: administering to the patient a therapeutically effective amount of a composition comprising α-lipoic acid and/or a salt thereof, and ambroxole and/or a salt thereof, wherein the patient's thiol-disulfide status is determined by the sum of all intracellular and all cell surface-located protein-bound and non-protein-bound thiol groups of a cell.

2. The method of claim 1, wherein the α-lipoic acid is administered in a dose of from about 30 mg/d to about 1200 mg/d.

3. The method of claim 1, wherein the α-lipoic acid is administered in a dose of from about 200 mg/d to about 600 mg/d.

4. The method of claim 1, wherein the ambroxole is administered in a dose of from about 7.5 mg/d to about 90 mg/d.

5. The method of claim 1, wherein the ambroxole is administered in a dose of from about 60 mg/d to about 75 mg/d.

6. The method of claim 1, wherein the composition is administered orally or parenterally.

7. The method of claim 1, wherein the composition further comprises an additive selected from the group consisting of aqueous solvents, stabilizers, suspending agents, dispersing agents, and wetting agents.

8. The method of claim 1, wherein the composition is administered in the form of a solution.

9. The method of claim 1, wherein the composition is administered in a solid form.

10. The method of claim 1, wherein the composition is administered during hemo- or peritoneal dialysis.

11. A method for treating a disturbance of a patient's thiol-disulfide status in a patient undergoing kidney replacement therapy, comprising: administering to the patient a therapeutically effective amount of a composition comprising α-lipoic acid and/or a salt thereof, and an ACE inhibitor selected from the group consisting of enalapril, captopril, ramipril, and mixtures thereof, wherein the patient's thiol-disulfide status is determined by the sum of all intracellular and all cell surface-located protein-bound and non-protein-bound thiol groups of a cell.

12. The method of claim 11, wherein the α-lipoic acid is administered in a dose of from about 30 mg/d to about 1200 mg/d.

13. The method of claim 11, wherein the ACE inhibitor is enalapril.

14. The method of claim 11, wherein the ACE inhibitor is captopril.

15. The method of claim 11, wherein the ACE inhibitor is ramipril.

16. The method of claim 11, wherein the ACE inhibitor is administered in a dose of from about 0.2 mg/d to about 20 mg/d.

17. The method of claim 11, wherein the composition is administered orally or parenterally.

18. The method of claim 11, wherein the composition further comprises an additive selected from the group consisting of aqueous solvents, stabilizers, suspending agents, dispersing agents, and wetting agents.

19. The method of claim 11, wherein the composition is administered in the form of a solution.

20. The method of claim 11, wherein the composition is administered in a solid form.

21. The method of claim 11, wherein the composition is administered during hemo- or peritoneal dialysis.

* * * * *